United States Patent [19]
Carden

[11] 4,201,737
[45] May 6, 1980

[54] NEBULIZING APPARATUS
[75] Inventor: Douglas D. Carden, Barneveld, Wis.
[73] Assignee: Airco, Inc., Montvale, N.J.
[21] Appl. No.: 938,284
[22] Filed: Aug. 30, 1978

Related U.S. Application Data

[63] Continuation-in-part of Ser. No. 816,110, Jul. 15, 1977, abandoned.

[51] Int. Cl.² .............................................. A61M 15/00
[52] U.S. Cl. ............................... 261/142; 128/200.21; 261/DIG. 65
[58] Field of Search ....................... 261/DIG. 65, 142; 128/192–194, 212; 220/250, 251, 314, 323, 325; 292/25, 55

[56] References Cited

U.S. PATENT DOCUMENTS

| | | | |
|---|---|---|---|
| 422,739 | 3/1890 | Darmstadt | 292/25 |
| 502,005 | 7/1893 | Mellor | 220/323 |
| 808,413 | 12/1905 | Wehrhahn | 292/55 |
| 1,439,000 | 12/1922 | Jacobs | 220/325 |
| 1,519,766 | 12/1924 | Demuth | 220/203 |
| 1,862,783 | 6/1932 | Burvenick | 292/25 |
| 2,195,132 | 3/1940 | Nelson | 220/325 |
| 2,522,718 | 9/1950 | Huck | 128/192 |
| 2,576,110 | 11/1951 | Fisher | 261/142 |
| 3,724,454 | 4/1973 | Brown | 261/DIG. 65 |
| 3,757,082 | 9/1973 | Goicoechea | 261/DIG. 65 |
| 3,806,102 | 4/1974 | Valenta et al. | 261/142 |
| 3,892,235 | 7/1975 | Van Amerongen | 128/194 |
| 4,028,444 | 6/1977 | Brown et al. | 128/193 |
| 4,036,919 | 7/1977 | Komendowski et al. | 261/DIG. 65 |

Primary Examiner—Frank W. Lutter
Assistant Examiner—Gregory N. Clements
Attorney, Agent, or Firm—Roger M. Rathbun; Edmund W. Bopp; Larry R. Cassett

[57] ABSTRACT

Improved nebulizing apparatus is disclosed for generating a heated liquid-dispensed-in-gas mist for administration to a patient undergoing aerosol therapy. The apparatus includes a novel fastening means for attaching a heater unit to the underside of a reservoir containing the liquid. The heater unit is easily attached and detached and yet enables good heat conductivity for heating the liquid within the interior of the reservoir. The bottom of the reservoir itself includes a concave heat conducting surface which, in operation, is in direct contact with the surface of the heater unit. The fastening means includes at least two draw clips which extend upwardly from the heater unit and which engage the reservoir to effect the desired fastening. By an adjustment of the draw clips with respect to the heater unit, the heat conducting surface of the reservoir can be forced out of its concavity to a flat, planar shape in good surface contact with the heater to enhance heat conductivity to liquid within the reservoir. The draw clips are held within stopping lugs on the reservoir to prevent rotation of the reservoir and thus preventing separation of the heat conducting surface from the remaining reservoir and accidental spillage of the hot liquid within the reservoir.

3 Claims, 6 Drawing Figures

U.S. Patent May 6, 1980 Sheet 3 of 3 4,201,737
FIG. 4
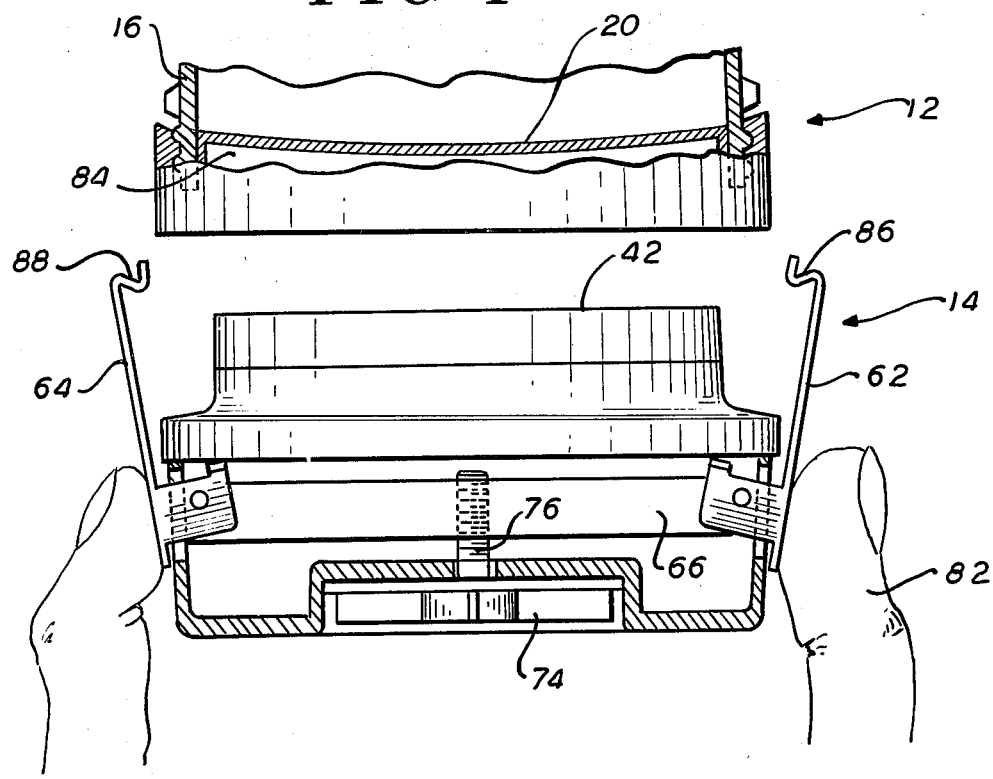
FIG. 5
FIG. 6
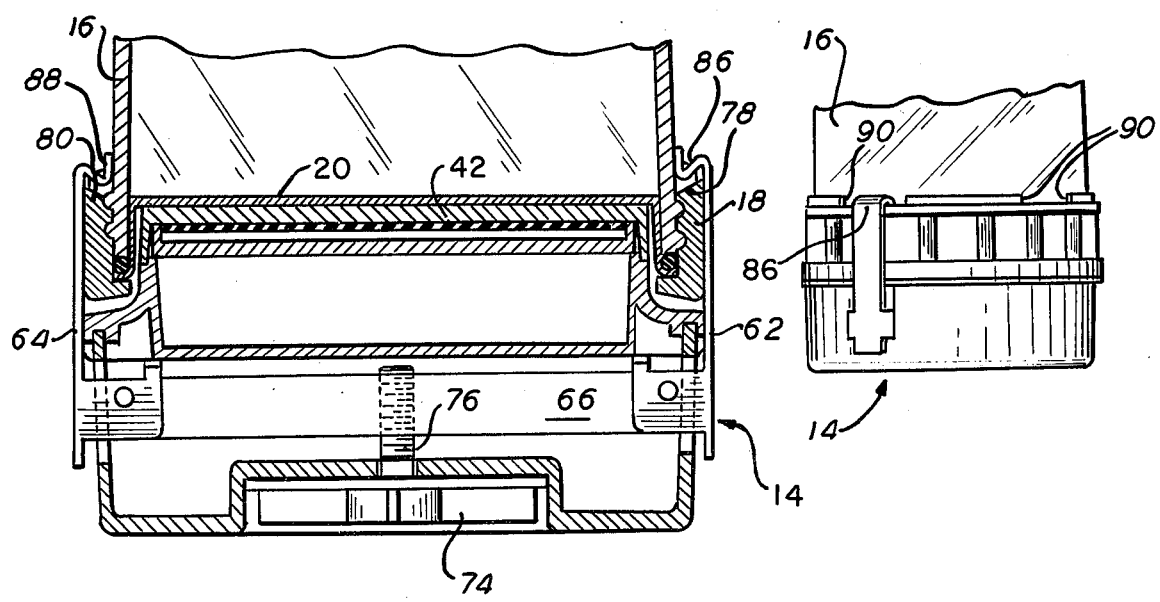

1

NEBULIZING APPARATUS

BACKGROUND OF INVENTION

This is a Continuation-in-Part of application Ser. No. 816,110, filed July 15, 1977, now abandoned.

This invention relates generally to medical treatment apparatus, and more specifically relates to nebulizing apparatus adapted to provide a heated liquid-in-gas mist for administering to a patient undergoing aerosol therapy.

In numerous medical procedures it is desirable to administer aerosol therapy to the patient undergoing treatment, and a large variety of apparatus has long been available for use in such procedures. In general such apparatus have comprised a reservoir for the water or aqueous solution of medicament which is to be dispersed in a gas—to form the desired mist. Thus in a typical mode of operation, a gas flow is supplied to a head assembly forming part of the nebulizer, and as is known in the art, a venturi passage or the like (in response to the gas flow) draws liquid from the reservoir into the nebulizer head, where it converges with a jet of gas forming a mist which is then impelled against an impact surface to separate larger liquid globules. The mist is discharged through an outlet port and thereupon furnished to the patient.

In numerous applications of aerosol therapy as described above, it is further desirable that the mist or aerosol furnished to the patient be heated—in order to insure salutory effects upon the patient. In prior apparatus such heating has usually been effected through use of an immersion heater or the like, commonly mounted or positioned at the bottom of the liquid reservoir, whereat the heater is in direct contact with the liquid. While this procedure is perfectly effective in achieving the objective of heating the liquid, a number of difficulties are thereby presented. A principal one is that the reservoir—which effectively is part of the patient treatment circuit—is in direct contact with the heating element; and since sterility is often a vital consideration in apparatus of the present type, it becomes necessary to sterilize not only the reservoir per se, but also the heating element and associated components which are mounted within the reservoir. This, however, is a relatively cumbersome procedure, which, among other things, can damage or impair the operation of the heating elements and possibly associated circuitry.

In numerous instances further, it would in principle be desirable to rapidly change the nature and composition of the mist output from a nebulizer; but in the aforementioned prior art arrangements this necessitates cleaning and sterilization of the entire apparatus, including the related heating portions thereof, which renders a rapid changeover impractical.

In certain apparatus disclosed in the prior art, the foregoing difficulties are substantially mitigated, by providing for completely separable reservoirs and heating units. Reference may especially be had in this connection to U.S. Pat. No. 3,806,102 to James D. Valenta et al, which patent is assigned to the assignee of the present application. The medical humidifier disclosed therein thus includes an overlying reservoir, which can be completely disassembled from the underlying heating unit as to enable ease of cleaning. The two units are adapted to interfit or nest with one another, and the overlying reservoir is provided with a central axial opening extending the length of the reservoir through which a tie bolt is passed and is threaded into a mating opening in the underlying heater. The tie bolt is then tightened to provide a relatively fixed stable relationship between the two units, and to somewhat improve heat conductivity between same.

While devices of this type disclosed in the aforementioned Valenta el al patent are indeed satisfactory for large humidifiers, the arrangement has several significant drawbacks in use with relatively small nebulzer apparatus. Such nebulizers are readily handled by one hand and ease of detaching and attaching the heater unit are facilitated.

In accordance with the foregoing it may therefore be regarded as an object of the present invention to provide nebulizing apparatus for generating a heated liquid-in-gas mist for administration to a patient, which apparatus includes separable reservoir and heating means, along with positive fastening means which are not only highly effective in assuring good thermal contact between the heating unit and reservoir, but which moreover, in association with other features of the invention, prevent accidental opening of the reservoir once same is operatively associated with the heating means, thereby precluding any possibility of accidental liquid discharge. In use, the heating unit is easily detachable from the reservoir by the use of one hand and is easily again attached by quick simple movements.

SUMMARY OF INVENTION

Now in accordance with the present invention, the foregoing object, and others as will become apparent in the course of the ensuing specification, are achieved in nebulizing apparatus which includes a reservoir, the bottom of which includes a thermally conductive concave or dished shape heat transfer plate for enabling heat conduction to liquid within the interior of the reservoir.

Modular heating means underlie the jar assembly and is in heat transmissive relationship to liquid within the reservoir by being in direct thermal contact with the heat transfer plate. Fastening means are provided for positively retaining the heating means in operative relation to the jar assembly—and thereby also promoting good thermal contact. Such fastening means comprise a pair of draw clips or dogs which are secured to and extend upwardly from the heating means. These draw clips are connected to a draw bar or cross-member which is axially displaceable by a torque knob recessed in the bottom of the heater housing. The operator by turning the said torque knob may draw the clips against a portion of the reservoir to thereby effect a firm contact between the heating means and the heat transfer plate which loses its concave shape and is forced into a flat, planar shape tightly held against the reservoir. The two modules when thus assembled, form a stable configuration, in that the heater module (now firmly attached to the reservoir) provides a stable base for the entire apparatus. The heater may be attached or removed by a simple one hand operation yet, through the use of the torque knob, the heater and reservoir are forcibly held against each other to provide good conduction between the heater means and the liquid within the reservoir.

The reservoir may include a reservoir jar closed at its bottom by a cap ring and gasket arrangement threadingly secured thereto. The draw clips specifically engage with the upwardly facing shoulder of the cap ring to effect the desired fastening. The reservoir jar may further include stopping lugs engageable by the lateral edges of the upwardly extending draw clips. This last feature prevents rotation of the cap ring with respect to the reservoir jar once the reservoir and heating means are secured to one another, to thereby preclude accidental opening of the reservoir and consequent liquid discharge.

BRIEF DESCRIPTION OF DRAWINGS

The invention is diagrammatically illustrated, by way of example, in the drawings appended hereto, in which:

FIG. 4 is an elevational sectional view, depicting the heating means and the bottom portions of the reservoir in the course of the two units being assembled;

FIG. 5 is a view similar to FIG. 4, depicting the heating means and reservoir in their assembled relation, but prior to full tightening of the torque knob; and FIG. 6 is a reduced scale external elevational view of the lower portion of the FIG. 1 apparatus.

DESCRIPTION OF PREFERRED EMBODIMENT

Figure 1:
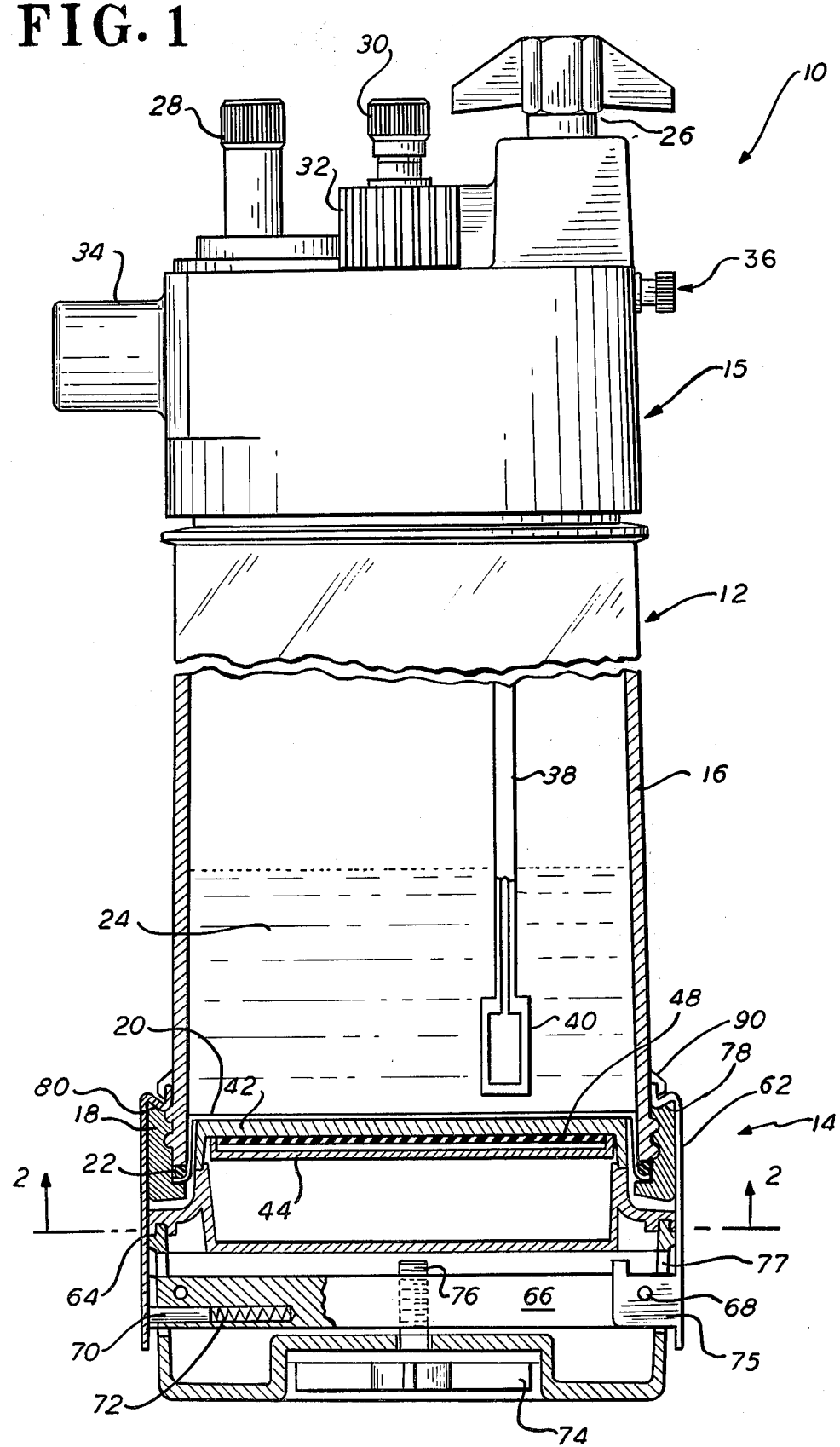
FIG. 1 is a side elevational view of apparatus in accordance with the present invention, with the lower portions thereof being broken away and sectioned in order to illustrate novel elements of the invention.

In FIG. 1 a side elevational view appears of apparatus in accordance with the present invention. The lower portions of this Figure are broken away and sectioned in order to illustrate novel elements of the invention.

Nebulizing apparatus 10 is seen to consist generally of a pair of what may be regarded as completely separable modules, viz. an upper module or reservoir 12, and an underlying module or heating means 14. In FIG. 1 these two modules are shown in their assembled, operative position. They are seen in disassembled, i.e. separated relationship in FIG. 4, which, in conjunction with FIG. 5 shows the manner in which the two are brought together by an operator.

In general, the upper portion of reservoir 12 comprises conventional elements. The novel elements of the present invention reside rather toward the bottom portions of reservoir 12, and in the heating means 14, which pursuant to the invention, is associated with the reservoir.

Thus referring to the reservoir 12: It is seen to comprise a jar assembly, consisting of a generally cylindrical chamber 16 (this chamber may slightly diverge toward the base thereof so as not to comprise, strictly speaking, a mathematical cylinder) which chamber is closed at its upper end by a nebulizer head assembly 15 which is threaded thereupon. Chamber 16 is closed at its lower end by a closure assembly including a cap ring 18 which is threaded upon the lower end of chamber 16, and which together with a heat transfer plate 20, and a gasket 22 provide a liquid-tight seal at the bottom of the reservoir, to prevent any leakage of liquid 24 contained within the interior of the reservoir. The heat transfer plate 20 is preferably concave or dished downwardly in its unassembled state.

Those elements associated with head assembly 15, and which serve to enable mixing of gas with the liquid contained in the reservoir and dispersion of such liquid in the gas to provide the desired mist, are conventional elements, and therefore are not set forth in any detail in connection with the present invention. Suffice it to point out that these conventional elements include the gas entry port 26 for gas which is to serve as the carrier for the desired mist, a diluter dial knob control 28 which by providing for an adjustable inflow of air adjusts the dilution of the gas proceeding via port 26 (where the latter is, for example, oxygen); a jet assembly, details of which cannot be seen in the drawing but which includes a clean-out knob 30 which can be removed to enable access to the said assembly; a fill port covered by cap 32 as seen in the drawing; and a mist outlet port 34. A clean-out plug is also seen at 36, which enables access to certain portions of the internal gas flow path.

As has previously been discussed, the general mode of operation of devices of the present type, is such that when a flow of gas is provided at a specified level, for example, typically in the range between about 5 and 12 liter/minute, a venturi or other arrangement enables development of a negative pressure in the tube 38 extending into liquid 24. The liquid is then drawn through filter 40, thence up tube 38 to nebulizer head assembly 15, where it is made to converge with a jet of the gas, and both impelled against an impact surface to form the mist which is discharged through outlet port 34.

In numerous therapeutic modes of operation, as has also been previously discussed, it is desirable that the said mist be at an elevated temperature. Typically, for example, it may be desired to provide such mist at temperatures of the order of 37° C. or so. In the present apparatus, the liquid 24 is completely isolated from the heating means 14, with substantially all heat flow to the liquid 24 being provided via the heat conducting interface established across the heat transfer plate 20—which comprises a metal having good chemical resistance as, for example, a relatively thin gauge stainless steel.

In particular, it is thus seen that in the assembled relationship between reservoir 12 and heating means 14, the said heat transfer plate 20 is maintained in face-to-face contact with a heater plate 42, forming the accessible, external heating portion of heater means 14—as may be seen, for example, in FIG. 4. Heat is actually provided to heater plate 42 by means of a heater assembly 48. This assembly is a relatively conventional type device (sometimes referred to as a "silicone heater") and consists of a photo-etched resistance grid which is sandwiched between two layers of insulating silicone rubber, and vulcanized to the bottom of the cast aluminum heater plate 42—which, as mentioned, constitutes the uppermost accessible element of heater means 14.

Figure 2:
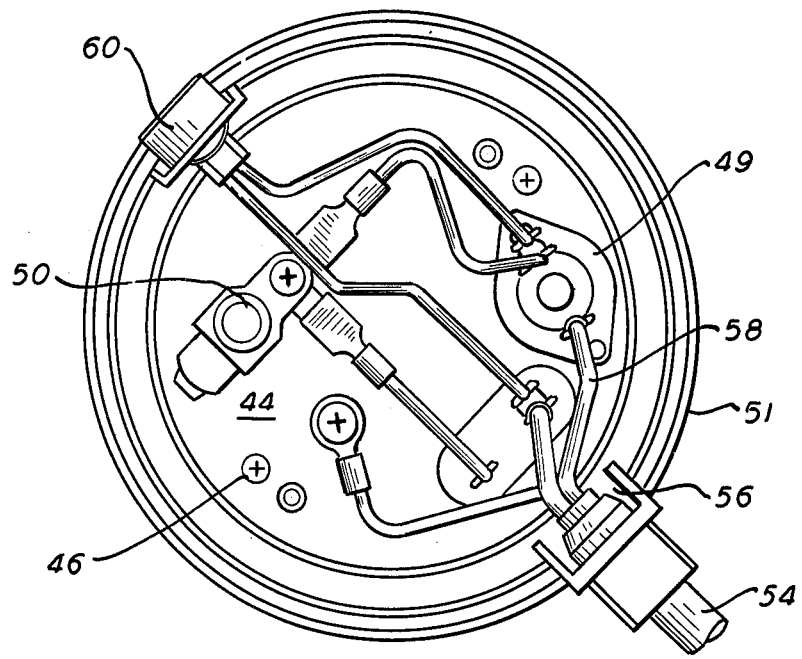
FIG. 2 is a plan view of the mounting plate portion of the heating means, the view being taken in the direction 2—2 of FIG. 1.
Figure 3:
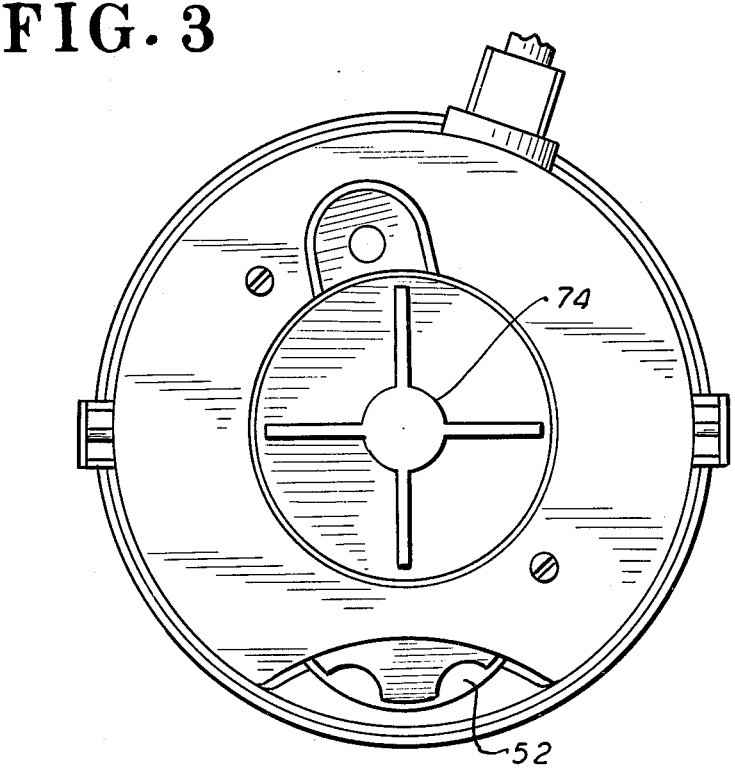
FIG. 3 is a bottom plan view of the FIG. 1 apparatus.

The internal mounting plate 44 secured to plate 42 by fasteners as at 46 is best seen in the plan view of FIG. 2. Mounting plate 44 carries various connectors and controls for heating means 14. These elements are per se conventional and are therefore only depicted in the present Figures in order to illustrate the mechanical relationship and arrangement with respect to the present device. Thus there is seen in FIG. 2 a limit thermostat 49, and control thermostat 50, each secured to the said mounting plate. Control thermostat 50 is mechanically linked with an external temperature control 52 which is mounted on the stem of thermostat 50. The control 52, which is setable by the operator, is seen in the bottom plan view of FIG. 3.

A 3-conductor power cord 54 enters the heater housing 51 through opening 56; a lead wire 58 thereof is connected to limit thermostat 49 which is typically preset to open the circuit should control thermostat 50 fail in a closed position and the heater temperature exceed some pre-selected value, typically about 149° C. A neon indicator light 60 is also provided; this extends through the heater housing 51, and is connected between the control thermostat 50 and limit thermostat 49 to indicate when electrical power is being supplied to the control thermostat.

Referring again to FIG. 1, it is seen that in the fully assembled position heat transfer plate 20 is indeed, as already discussed, in face-to-face contact with heater plate 42, to enable effective heat transfer to liquid 24. Reservoir 12 and heating means 14 are maintained in their desired relationship by means of a pair of dogs or draw clips 62 and 64. Each of these draw clips is hinged to a cross-member 66 by a pin 68, and are further springloaded by a second pin 70 and spring 72, which thus serve to automatically lock the draw clips 62, 64 over the threaded cap ring 18 secured to the bottom of the reservoir. When the clips 62, 64 are thus emplaced, a torque knob 74 (FIG. 3) is turned clockwise by the operator. The threaded shank 76 extending from this torque knob passes through a threaded opening in cross member 66, which as the knob is advanced therefor serves to withdraw (i.e. lower) the cross member 66. As the arm portions 75 of clips 62, 64 extend through vertical slots 77 in housing 51, the said clips are vertically displaced with member 66. Thus the draw clips 62 and 64 are withdrawn (i.e. pulled downwardly with cross member 66), and thereupon firmly engage the uppermost shoulders 78 and 80 of ring 18. This in turn draws the entire heating means 14, and specifically heater plate 42 into firm face-to-face contact with heat transfer plate 20, to achieve the configuration depicted in FIG. 1. In so forcing the heat transfer plate 20 against the flat surface of heater plate 42, the heat transfer plate 20 loses its concave or dished shape and is uniformly pressed against heater plate 42, thus better overall physical contact is obtained than forcing two flat surfaces against each other. When the concave shape of heat transfer plate 20 is forced to a flat, planar configuration, almost the entire surface contacts heater plate 42 to insure optimum heat transmission.

The assembly sequence, i.e. assembly of the modules 12 and 14 with respect to one another, may be better appreciated by referring to FIGS. 4 and 5. Thus in FIG. 4 reservoir 12 and heating means 14 are shown in their separated states, with the operator whose fingers are indicated at 82, shown in the course of depressing the lower portions of draw clips 62, 64 against the spring biasing forces previously discussed. In consequence of this action the upper portions of the clips are displaced outwardly from the axis of the apparatus. It should, incidentally, be noted here, that such operation is enabled in very simple fashion—indeed by simple one hand operation.

The reservoir 12 and heating means 14 are then brought into nesting relationship, as in FIG. 5, in which Figure clips 62, 64 have been released by the operator. Thus it is seen from FIG. 5 that while the two modules are nested with respect to one another with the uppermost portion of heating means 14 including heater plate 42 being received into the well-like portion 84 (FIG. 4) defined at the bottom of reservoir 12, it is nevertheless seen that the uppermost engaging portions 86 and 88 of the draw clips are not yet in contact with shoulders 78 and 80 of ring 18, in consequence of which there is not complete assurance that a firm-face-to-face contact has indeed been effected between heater plate 42 and the heat transfer plate 20. Thus the depiction of FIG. 5 precedes the final assembly configuration shown in FIG. 1, which, as already mentioned, is achieved from the FIG. 5 arrangement by actuation of the torque knob 74—as already discussed.

When the final configuration depicted in FIG. 1 is thus achieved, the stopping lugs 90, which are molded or otherwise formed as a series of elements circumferentially spaced about the lower periphery of chamber 16, serve to prevent ring 18 from being removed. This may be better appreciated by simultaneous reference to the external view of FIG. 6, from whence it is seen that the engaging portion 86 is nested into the spaces between lugs 90. In consequence the lateral edges of the portion 86 will abut the lugs 90 if any attempt is made to inadvertently unscrew the chamber 16 from cap 18. This is important, since once the assembly of FIG. 1 is achieved, and the apparatus placed into operation, the reservoir may contain a full charge of warm liquid. By virtue of the present arrangement the danger posed by accidental opening of the reservoir is thus eliminated.

When apparatus 10 is thus assembled (as in FIG. 1), it will be clear further that a completely safe and stable structure is enabled, with the underlying heating means 14 serving as a firm and secure base for the overall apparatus. At the same time it will be evident that the simplicity of interengaging the reservoir and heating means with respect to one another, and the equal ease with which they may be disengaged, enables ready removal of the reservoir 12—which can then be cleaned or sterilized or the like. It will further be evident that at all times the underlying heating means 14 is completely isolated from any liquid 24 contained in reservoir 12; in consequence of which there is no necessity for sterilizing or otherwise treating the said heating means from a medical viewpoint. The construction further, again by virtue of its ready disengagement and engagement, enables an operator to utilize one or more heating means interchangeably with reservoir containing differing solutions or so forth.

While the present invention has been particularly described in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

I claim:

1. Nebulizer apparatus for generating a heated liquid-in-gas mist for administration to a patient in the course of aerosol therapy; said apparatus comprising in combination:

reservoir means for containing liquid to be dispersed in said gas; gas inlet means for providing an input of gas to said apparatus; means for mixing said liquid with said gas to form said mist;

mist outlet means for providing said mist toward said patient;

a normally downwardly concave thermally conductive heat transfer plate forming the bottom of said reservoir means; heating means underlying said reservoir means for heating said liquid, said heating means being separable from said reservoir and having a substantially flat surface;

fastening means for positively retaining said heating means in operative association with said reservoir in heat transmissive relationship with said heat transfer plate, said fastening means comprising draw clips secured to and extending upwardly from said heating means and being engaged with said reservoir means, and adjusting means adapted to move said draw clips to draw said heat transfer plate tightly against said substantially flat surface of said heating means to cause said heat transfer plate to lose its downward concavity and assume a substantially flat configuration against said heating means to establish and maintain good thermal contact therebetween.

2. Apparatus in accordance with claim 1, wherein said reservoir means includes a generally cylindrical chamber and said liquid-tight means closing the bottom of said reservoir includes a cap ring threadingly secured to the bottom of said chamber; a series of stopping lugs being formed on the external surface of said cylindrical chamber wall adjacent said cap ring and being spaced with respect to one another about the circumference of said chamber; said draw clips being seatable upon the said cap and nesting between said lugs, and said lugs thereby blocking rotation of said cylindrical chamber when said clips are in said seated position, thereby preventing accidental rotation of said cap with consequent liquid discharge when said reservoir and underlying heater are in operative relationship.

3. Apparatus in accordance with claim 1, wherein said means closing the bottom of said reservoir means defines an upwardly-extending well-like portion bounded by said heat transfer plate, said heating means being received in nested fashion in said well-like portion.

* * * * *